(12) United States Patent
Nomura et al.

(10) Patent No.: US 12,184,038 B2
(45) Date of Patent: Dec. 31, 2024

(54) LASER APPARATUS

(71) Applicant: FURUKAWA ELECTRIC CO., LTD., Tokyo (JP)

(72) Inventors: Yoshiki Nomura, Tokyo (JP); Shunichi Matsushita, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 657 days.

(21) Appl. No.: 17/478,193

(22) Filed: Sep. 17, 2021

(65) Prior Publication Data

US 2022/0006266 A1  Jan. 6, 2022

Related U.S. Application Data

(63) Continuation of application No. PCT/JP2020/013017, filed on Mar. 24, 2020.

(30) Foreign Application Priority Data

Mar. 27, 2019 (JP) .................................. 2019-060396

(51) Int. Cl.
*H01S 3/00* (2006.01)
*H01S 5/00* (2006.01)
(Continued)

(52) U.S. Cl.
CPC ............ *H01S 5/4012* (2013.01); *H01S 5/005* (2013.01); *H01S 5/0239* (2021.01);
(Continued)

(58) Field of Classification Search
CPC ...... H01S 5/4012; H01S 5/005; H01S 5/0239; H01S 5/4025; H01S 5/02251; H01S 2301/206
See application file for complete search history.

(56) References Cited

U.S. PATENT DOCUMENTS 4,981,138 A * 1/1991 Deckelbaum .......... A61B 18/24
                                                                600/478
5,949,932 A * 9/1999 Lawrenz-Stolz ...... A61B 18/22
                                                                385/33
(Continued)

FOREIGN PATENT DOCUMENTS

JP      2005-157225 A    6/2005
JP      2007-41342 A     2/2007
(Continued)

OTHER PUBLICATIONS

Japanese Office Action issued Aug. 9, 2022 in Japanese Application No. 2019-060396 (with unedited computer generated English Translation), 6 pages.
(Continued)

*Primary Examiner* — Kinam Park
(74) *Attorney, Agent, or Firm* — Oblon, McClelland, Maier & Neustadt, L.L.P.

(57) ABSTRACT

A laser apparatus includes: one or more laser diodes and two or more optical combiners. Further, output sides of the one or more laser diodes are connected to an input side of one optical combiner among the two or more optical combiners, and an output side of the one optical combiner is connected to an input side of an optical combiner other than the one optical combiner.

9 Claims, 4 Drawing Sheets

(51) Int. Cl.
    *H01S 5/0239*     (2021.01)
    *H01S 5/40*     (2006.01)
    *G02B 6/42*     (2006.01)
    *H01S 5/02251*     (2021.01)

(52) U.S. Cl.
    CPC ............ *H01S 5/4025* (2013.01); *G02B 6/425* (2013.01); *G02B 6/4287* (2013.01); *H01S 5/02251* (2021.01); *H01S 2301/206* (2013.01)

(56) References Cited

U.S. PATENT DOCUMENTS

| | | | |
|---|---|---|---|
| 6,212,310 B1* | 4/2001 | Waarts | H04B 10/291 |
| | | | 385/127 |
| 6,275,632 B1 | 8/2001 | Waarts et al. | |
| 6,298,187 B1 | 10/2001 | Waarts et al. | |
| 6,411,323 B1 | 6/2002 | Waarts et al. | |
| 6,785,440 B1* | 8/2004 | Lawrenz-Stolz | G02B 6/4249 |
| | | | 385/33 |
| 10,543,378 B2 | 1/2020 | Tagliaferri et al. | |
| 10,845,032 B2 | 11/2020 | Jutte et al. | |
| 2004/0247011 A1* | 12/2004 | Okazaki | G02B 19/0095 |
| | | | 372/108 |
| 2006/0002649 A1 | 1/2006 | Murphy et al. | |
| 2006/0002650 A1 | 1/2006 | Vokey et al. | |
| 2007/0086693 A1 | 4/2007 | Murphy et al. | |
| 2007/0092176 A1 | 4/2007 | Murphy et al. | |
| 2007/0116400 A1 | 5/2007 | Murphy et al. | |
| 2011/0261456 A1* | 10/2011 | Raab | H01S 3/082 |
| | | | 359/489.08 |
| 2015/0272679 A1* | 10/2015 | Wang | A61B 18/24 |
| | | | 606/15 |
| 2018/0059323 A1 | 3/2018 | Rivera et al. | |
| 2018/0059425 A1 | 3/2018 | Rivera et al. | |
| 2019/0041579 A1 | 2/2019 | Daidoji et al. | |
| 2020/0197093 A1 | 6/2020 | Wang et al. | |

FOREIGN PATENT DOCUMENTS

| | | |
|---|---|---|
| JP | 2018-521478 A | 8/2018 |
| JP | 2018-534110 A | 11/2018 |
| WO | WO 2017/175391 A1 | 10/2017 |

OTHER PUBLICATIONS

Combined Chinese Office Action and Search Report issued Jul. 22, 2023 in Chinese Application 202080022691.9 (with unedited computer-generated English translation), 12 pages.

International Search Report issued Jun. 23, 2020 in PCT/JP2020/013017, filed on Mar. 24, 2020, 2 pages.

Extended European Search Report issued Nov. 21. 2022, in corresponding European Patent Application No. 20777511.5, 8 pages.

* cited by examiner

LASER APPARATUS

CROSS-REFERENCE TO RELATED APPLICATION(S)

This application is a continuation of International Application No. PCT/JP2020/013017, filed on Mar. 24, 2020 which claims the benefit of priority of the prior Japanese Patent Application No. 2019-060396, filed on Mar. 27, 2019, the entire contents of which are incorporated herein by reference.

BACKGROUND

The present disclosure relates to a laser apparatus.

There is a known laser apparatus for providing a medical treatment by inserting a catheter into the patient's body and irradiating a target area, such as an affected area, with a laser light from the tip of an optical fiber inside the catheter. In such ablation by a laser light, there is a case where a beam of a laser light high in flatness of the beam profile is used, other than Gaussian light. Note that, hereinafter, the flatness of the beam profile of a laser light will be simply referred to as "laser light flatness".

As a technique for improving such laser light flatness, for example, Japanese Laid-open Patent Publication No. 2005-15722 discloses a configuration that improves the laser light flatness by inputting lights guided through a plurality of optical waveguides into the incident end of an optical transmitter, and transmitting the lights while confining the lights in the optical transmission region of the optical transmitter.

In addition, Japanese Translation of PCT International Application Publication No. 2018-534110 discloses a configuration for converting a Gaussian beam at a multi-mode optical fiber output into a flat top beam. Further, Japanese Translation of PCT International Application Publication No. 2018-521478 discloses a configuration equipped with a beam shaping optical element that redistributes the light emitted by a high-brightness light source into an emission optical beam having a far-field beam sectional profile with a spatially flat optical intensity distribution.

SUMMARY

There is a need for providing a laser apparatus that is excellent in space saving property and can improve the laser light flatness.

According to an embodiment, a laser apparatus includes: one or more laser diodes and two or more optical combiners. Further, output sides of the one or more laser diodes are connected to an input side of one optical combiner among the two or more optical combiners, and an output side of the one optical combiner is connected to an input side of an optical combiner other than the one optical combiner.

DETAILED DESCRIPTION

In the related art, the configuration disclosed in each of Japanese Laid-open Patent Publication No. 2005-15722 and Japanese Translation of PCT International Application Publication Nos. 2018-534110 and 2018-521478 entails problems in that, for example, the configuration cannot be used in a thin tube, such as a medical catheter or the like, because the apparatus configuration is complicated or requires a large placement space.

A laser apparatus according to the present disclosure will be explained below with reference to the accompanying drawings. Note that the present disclosure is not limited to the following embodiments. Further, the constituent elements in the following embodiments encompass those which can be easily used as replacements by a person skilled in the art, or which are substantially equivalent thereto.

A laser apparatus according to the present disclosure is characterized in that the laser apparatus includes one or more ablation-related laser diodes (each of which will be referred to as "ablation-related LD", hereinafter) and two or more optical combiners, and that the optical combiners are connected to each other in series (cascade connection). Hereinafter, explanations will be given of embodiments of a laser apparatus according to the present disclosure, with reference to FIGS. 1 to 5.

FIRST EMBODIMENT

Figure 1:
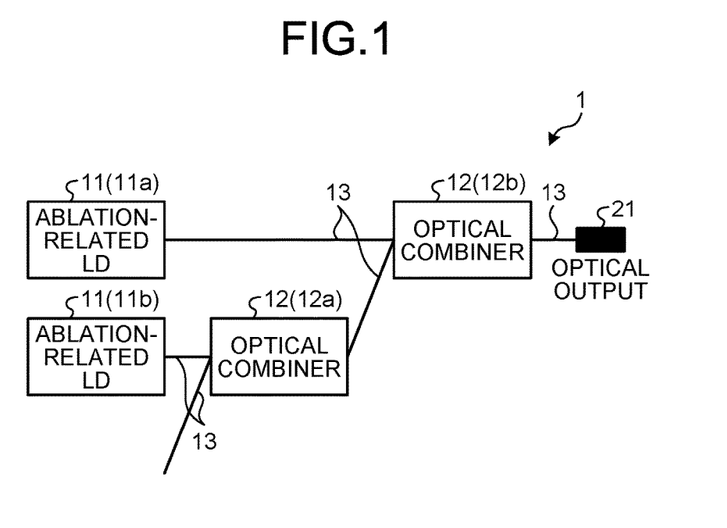
FIG. 1 is a schematic diagram illustrating the configuration of a laser apparatus according to a first embodiment of the present disclosure.

A laser apparatus 1 according to this embodiment includes, as illustrated in FIG. 1, two ablation-related LDs 11a and 11b, two optical combiners 12a and 12b, and optical fibers 13 arranged between the ablation-related LDs 11a and 11b and the optical combiners 12a and 12b. Note that, in the following descriptions, the plurality of ablation-related LDs are expressed as "ablation-related LDs 11" when being collectively referred to, and the plurality of optical combiners are expressed as "optical combiners 12", when being collectively referred to.

When the laser apparatus 1 is used for a laser medical treatment by a medical catheter, the ablation-related light output from each ablation-related LD 11 is a light in a wavelength bandwidth, which is the so-called "living window", that is, a light in a wavelength bandwidth of 600 nm to 1,500 nm. Further, the output of each ablation-related LD 11 is set to 0.1 W or more, for example. Here, the respective ablation-related LDs 11 may be connected to each other, for example, in series, and may be configured to be supplied with a common current from the same power supply, or may be configured to be supplied with different currents from separate power supplies. In this respect, when the ablation-related LDs 11 are supplied with currents from separate power supplies, there is an advantage that the mixing ratio of the laser lights from the respective ablation-related LDs 11 can be changed.

The ablation-related LD 11a is connected to the input side of the optical combiner 12b via an optical fiber 13. Further, the ablation-related LD 11b is connected to the input side of the optical combiner 12a via an optical fiber 13. The optical fiber 13 used as the output port of each ablation-related LD 11 is formed of a multi-mode optical fiber or single-mode optical fiber. Here, the length of the optical fiber 13 is about 1 m, for example.

Figure 2:
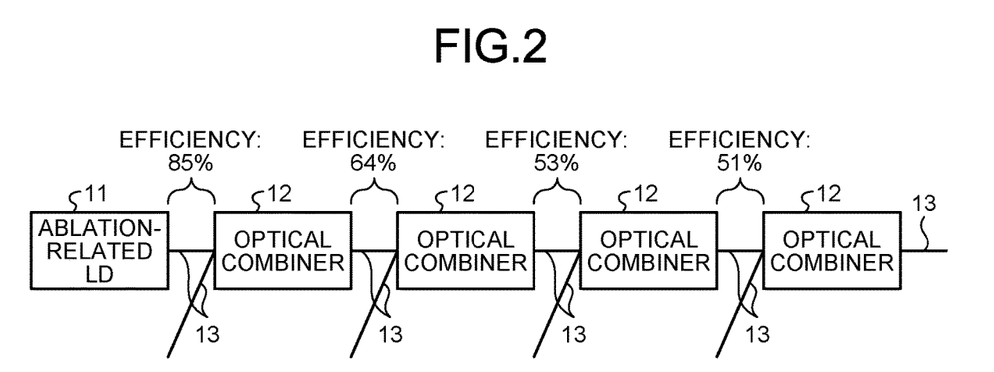
FIG. 2 is an explanatory diagram for explaining the efficiency in a case where optical combiners are connected in a plurality of stages.

Now, as illustrated in FIG. 2, when a plurality of optical combiners 12 are connected in a cascade state, as the number of stages of this cascade connection is larger, the efficiency (the power of the laser light) becomes lower. Therefore, as illustrated in FIG. 1, the two ablation-related LDs 11 are individually connected to the separate optical combiners 12, and, further, the number of ablation-related LDs 11 connected to each optical combiner 12 is minimized, by which the decrease in the efficiency can be suppressed. Further, when the two ablation-related LDs 11 are individually connected to the separate optical combiners 12, lights that have been made different in propagation mode type are mixed by the optical combiner 12 in the subsequent stage, and the laser light flatness is thereby improved.

The number of ablation-related LDs 11 is preferably smaller than the total number of input ports of the optical combiners 12. In other words, the optical combiners 12 preferably include one or more input ports to which no ablation-related LD 11 is connected. Here, the "input port" means a port other than the port connected to another optical combiner 12 among the ports on the input side of each optical combiner 12. The laser apparatus 1 illustrated in FIG. 1 is configured such that the number of ablation-related LDs 11 is two, and the total number of input ports of the optical combiners 12 is three.

Each of the optical combiners 12 serves to multiplex (synthesize) a plurality of lights. Each of the optical fibers 13 used as the input port and the output port of each optical combiner 12 is formed of a multi-mode optical fiber. This optical fiber 13 has, for example, a core diameter of 105 µm and a clad diameter of 125 µm, and is composed of a step-index type optical fiber including a coating, such as an acrylate coating film or polyimide coating film.

Each of the optical combiners 12 is an N:1 optical combiner, and preferably a 2:1 optical combiner. Further, each optical combiner 12 is a combiner of an end couple type or side couple type. Further, the respective optical combiners 12 are mounted on the same plate made of a metal. This metal plate also functions as a heat dissipation plate.

The output side of the optical combiner 12a is connected to the input side of the optical combiner 12b via an optical fiber 13. Further, the output side of the optical combiner 12b is connected to an optical output section 21 via an optical fiber 13. Here, as regards the vacant port of the optical combiner 12a to which no ablation-related LD 11 is connected, a light source (for example, a monitor-related LD or the like) other than the ablation-related LDs 11 may be connected thereto.

As described above, when the plurality of optical combiners 12 are connected in a cascade state, as the number of stages of this cascade connection is larger, the efficiency (the power of the laser light) becomes lower. Therefore, as illustrated in FIG. 1, the number of continuous connection stages of the optical combiners 12 is set to be not more than two, by which the decrease in the efficiency can be suppressed as much as possible. Further, there is a case where the optical combiner 12 connected to the subsequent stage generates heat as the efficiency decreases. Therefore, the optical combiner 12b, which is in the subsequent stage, of the optical combiners 12a and 12b, may be equipped with a heat dissipation mechanism (for example, a heat dissipation plate) to suppress heat generation.

The optical output section 21 serves to output the light multiplexed by the optical combiner 12b. The specific configuration of the optical output section 21 depends on the application of the laser apparatus 1. For example, when the laser apparatus 1 is used for a laser medical treatment by a medical catheter, the optical output section 21 is composed of an optical probe or the like.

In the laser apparatus 1 configured as described above, since the plurality of optical combiners 12a and 12b are connected in a cascade state, it is possible to improve the laser light flatness without requiring a large space. Further, in the laser apparatus 1, since the two ablation-related LDs 11a and 11b are individually connected to the separate optical combiners 12a and 12b, lights that have been made different in propagation mode type are mixed by the optical combiner 12b in the subsequent stage, so it is possible to improve the laser light flatness.

In addition, for example, in the configuration disclosed in Japanese Translation of PCT International Application Publication No. 2018-534110 mentioned above, it is necessary to use an optical fiber with a length of 5 m or more in order to convert the mode of a laser light. However, in the laser apparatus 1 according to this embodiment, since the mode of laser light is converted by the optical combiners 12, it is not necessary to elongate the optical fibers 13. Therefore, the laser apparatus 1 can achieve space saving more than the configuration disclosed in Japanese Translation of PCT International Application Publication No. 2018-534110.

SECOND EMBODIMENT

Figure 3:
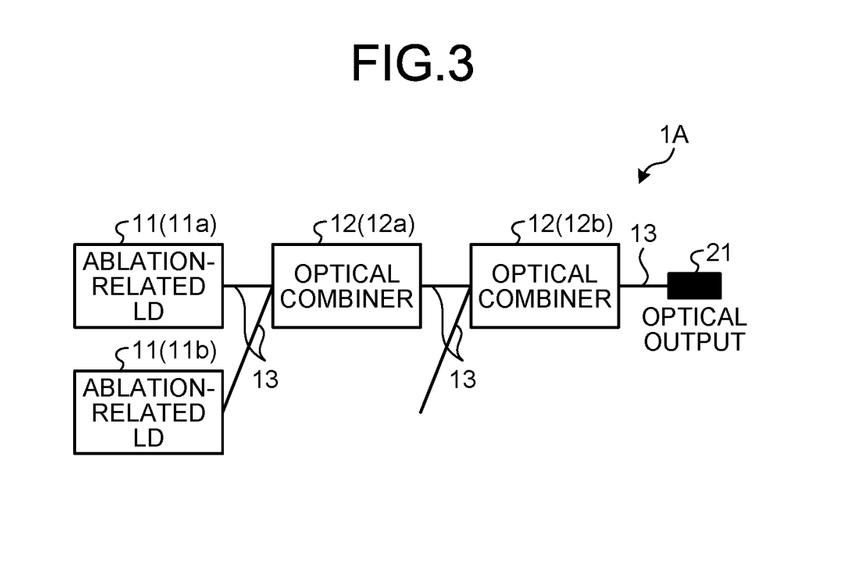
FIG. 3 is a schematic diagram illustrating the configuration of a laser apparatus according to a second embodiment of the present disclosure.

A laser apparatus 1A according to this embodiment includes, as illustrated in FIG. 3, two ablation-related LDs 11a and 11b, two optical combiners 12a and 12b, and optical fibers 13 arranged between the ablation-related LDs 11a and 11b and the optical combiners 12a and 12b. Here, the configurations of the ablation-related LDs 11, the optical combiners 12, the optical fibers 13, and the optical output section 21, illustrated in FIG. 3, are the same as those of the first embodiment described above.

The ablation-related LDs 11a and 11b are connected to the input side of the optical combiner 12a via optical fibers 13. Further, the output side of the optical combiner 12a is connected to the input side of the optical combiner 12b via an optical fiber 13. Further, the output side of the optical combiner 12b is connected to the optical output section 21 via an optical fiber 13. In this way, in the laser apparatus 1A according to this embodiment, the two ablation-related LDs 11a and 11b are connected to the input side of the same optical combiner 12a, and no ablation-related LD 11 is connected to the optical combiner 12b arranged in the second stage.

In the laser apparatus 1A configured as described above, since the plurality of optical combiners 12a and 12b are connected in a cascade state, it is possible to improve the laser light flatness without requiring a large space.

THIRD EMBODIMENT

Figure 4:
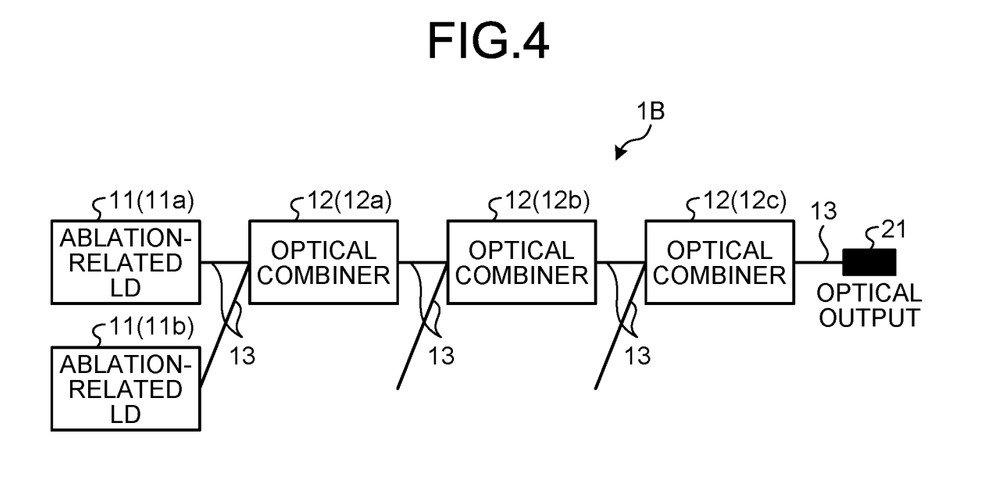
FIG. 4 is a schematic diagram illustrating the configuration of a laser apparatus according to a third embodiment of the present disclosure.

A laser apparatus 1B according to this embodiment includes, as illustrated in FIG. 4, two ablation-related LDs 11a and 11b, three optical combiners 12a, 12b, and 12c, and optical fibers 13 arranged between the ablation-related LDs 11a and 11b and the optical combiners 12a, 12b, and 12c. Here, the configurations of the ablation-related LDs 11, the optical combiners 12, the optical fibers 13, and the optical output section 21, illustrated in FIG. 4, are the same as those of the first embodiment described above.

The ablation-related LDs 11a and 11b are connected to the input side of the optical combiner 12a via optical fibers 13. Further, the output side of the optical combiner 12a is connected to the input side of the optical combiner 12b via an optical fiber 13. Further, the output side of the optical combiner 12b is connected to the input side of the optical combiner 12c via an optical fiber 13. Further, the output side of the optical combiner 12c is connected to the optical output section 21 via an optical fiber 13. In this way, in the laser apparatus 1B according to this embodiment, the number of continuous connection stages of the optical combiners 12 is three.

In the laser apparatus 1B configured as described above, since the plurality of optical combiners 12a and 12b are connected in a cascade state, it is possible to improve the laser light flatness without requiring a large space. Further, in the laser apparatus 1B, since the number of continuous connection stages of the optical combiners 12 is three, higher-order modes can be excited at the respective optical combiners 12. Therefore, as compared to a case where the number of continuous connection stages of the optical combiners 12 is set to two or less, it is possible to obtain a laser light with more higher-order modes.

FOURTH EMBODIMENT

Figure 5:
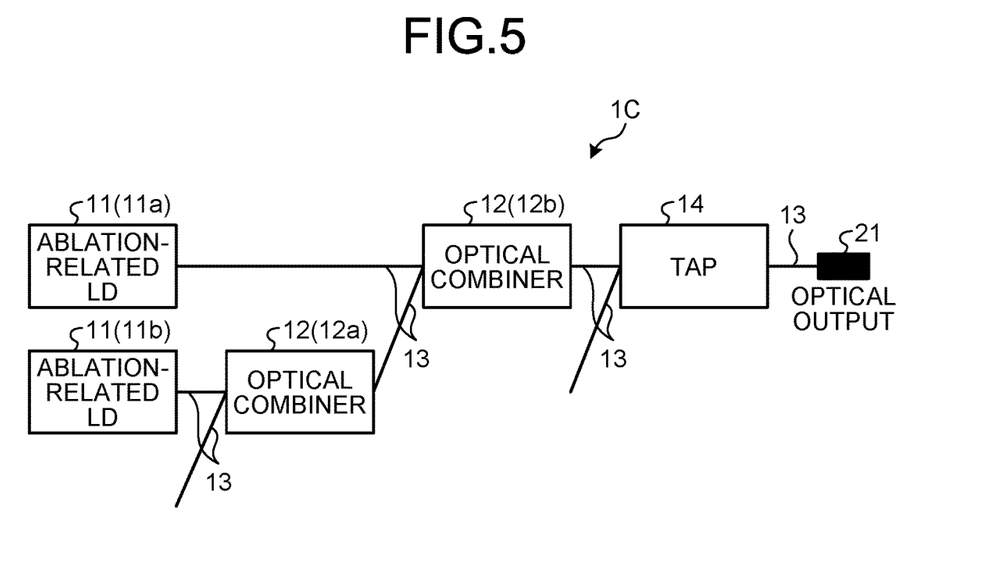
FIG. 5 is a schematic diagram illustrating the configuration of a laser apparatus according to a fourth embodiment of the present disclosure.

A laser apparatus 1C according to this embodiment includes, as illustrated in FIG. 5, two ablation-related LDs 11a and 11b, two optical combiners 12a and 12b, optical fibers 13 arranged between the ablation-related LDs 11a and 11b and the optical combiners 12a and 12b, and an asymmetric tap coupler 14. Here, the configurations of the ablation-related LDs 11, the optical combiners 12, the optical fibers 13, and the optical output section 21, illustrated in FIG. 5 are the same as those of the first embodiment described above.

The ablation-related LD 11a is connected to the input side of the optical combiner 12b via an optical fiber 13. Further, the ablation-related LD 11b is connected to the input side of the optical combiner 12a via an optical fiber 13. Further, the output side of the optical combiner 12a is connected to the input side of the optical combiner 12b via an optical fiber 13. Further, the output side of the optical combiner 12b is connected to the input side of the asymmetric tap coupler 14 via an optical fiber 13.

Further, the output side of the asymmetric tap coupler 14 is connected to the optical output section 21 via an optical fiber 13. In this way, in the laser apparatus 1C according to this embodiment, the optical combiner 12b arranged in the rearmost stage is provided with the asymmetric tap coupler 14.

The composition ratio of the asymmetric tap coupler 14 can be set to, for example, 99:1, 95:5, 90:10, 75:25, etc.

Further, in the asymmetric tap coupler 14 illustrated in FIG. 5, the ratio of input ports to output ports is 2:1, but the ratio of input ports to output ports may be set to 1:2 or 2:2. Here, as regards the vacant port of the asymmetric tap coupler 14, for example, a light source, such as a monitor-related PD or the like, which outputs a wavelength different from those of the ablation-related LDs 11, may be connected thereto.

In the laser apparatus 1C configured as described above, since the plurality of optical combiners 12a and 12b are connected in a cascade state, it is possible to improve the laser light flatness without requiring a large space. Further, in the laser apparatus 1C, since the asymmetric tap coupler 14 is connected to the optical combiner 12b in the rearmost stage, the higher-order mode light excited by the optical combiner 12b is removed by the asymmetric tap coupler 14, and a ring beam is formed from the position of the tap port. Consequently, the light at the main port can be rid of higher-order mode light at a rate depending on the composition ratio, so it is possible to further improve the flatness.

Hereinafter, the present disclosure will be described more specifically by taking working examples. First, an explanation will be given of the relationship of the number of optical combiners with the laser light flatness and intensity in a laser apparatus in which the optical combiners are connected in a cascade state, with reference to Table 1. Here, in general, as the full width at half maximum in the intensity distribution in the beam profile (which will be simply referred to as "full width at half maximum", hereinafter) of a laser light is smaller, the flatness tends to be higher. Therefore, in the following explanation, the full width at half maximum is used as an index to judge the laser light flatness.

TABLE 1

| No. | Number of optical combiners | Full width at half maximum | Optical intensity maximum value |
|---|---|---|---|
| 1 | 0 | 1.19 | 8.51 |
| 2 | 1 | 1.15 | 8.34 |
| 3 | 2 | 1.12 | 8.00 |
| 4 | 3 | 1.38 | 7.75 |

As illustrated in Table 1, the full width at half maximum of a laser light decreases in the order of Nos. 4, 1, 2, and 3. Specifically, when the number of optical combiners is zero to two, as the number of optical combiners is larger, the full width at half maximum is smaller and the flatness is higher. On the other hand, when the number of optical combiners is three, the full width at half maximum is larger than that of when the number of optical combiners is zero. This is because the optical combiner has a mode converter function that excites a higher-order mode light, and, when the number of optical combiners exceeds a certain level, the ratio of higher-order mode lights is increased and the flatness is deteriorated. Here, the number of optical combiners that deteriorates the flatness also depends on the characteristics of the optical combiners.

Further, as illustrated in Table 1, the optical intensity maximum value of a laser light decreases in the order of Nos. 1, 2, 3, and 4, that is, the value is smaller as the number of optical combiners is larger.

Next, an explanation will be given of the relationship of the connection method of ablation-related LDs and the number of optical combiners with the laser light flatness and intensity in a laser apparatus in which the optical combiners are connected in a cascade state, with reference to Table 2.

TABLE 2

| No. | LD connection method | Number of optical combiners | Full width at half maximum | Optical intensity maximum value |
|---|---|---|---|---|
| 5 | — | 0 | 1.19 | 8.51 |
| 6 | Parallel connection | 1 | 1.15 | 8.34 |
| 7 | Parallel connection | 2 | 1.12 | 8.00 |
| 8 | Individual connection | 2 | 1.09 | 8.05 |
| 9 | Parallel connection | 3 | 1.38 | 7.75 |
| 10 | Individual connection | 3 | 0.983 | 7.82 |

Here, Nos. 5 to 10 in Table 2 represent the following configurations, respectively.

No. 5 represents a configuration in which only one ablation-related LD is arranged and no optical combiner is included.

No. 6 represents a configuration in which two ablation-related LDs are connected to one optical combiner.

No. 7 represents the configuration of FIG. 3.

No. 8 represents the configuration of FIG. 1.

No. 9 represents the configuration of FIG. 4.

No. 10 represents a configuration in which the ablation-related LDs 11 are individually connected to the respective input sides of the optical combiners 12 in FIG. 4.

As illustrated in Table 2, the full width at half maximum of a laser light decreases in the order of Nos. 9, 5, 6, 7, 8, and 10. Specifically, the configuration, in which the number of continuous connection stages of optical combiners is three and the ablation-related LDs are individually connected to the respective input sides of the optical combiners in the first stage and the second stage, is the smallest in the full width at half maximum and thus is the highest in the flatness.

Further, as illustrated in Table 2, the optical intensity maximum value of a laser light decreases in the order of Nos. 5, 6, 8, 7, 10, and 9. Specifically, the configuration (see FIG. 4), in which the number of continuous connection stages of optical combiners is three and the two ablation-related LDs are connected to the input side of the optical combiner in the first stage, is the smallest in the optical intensity.

Figure 6:
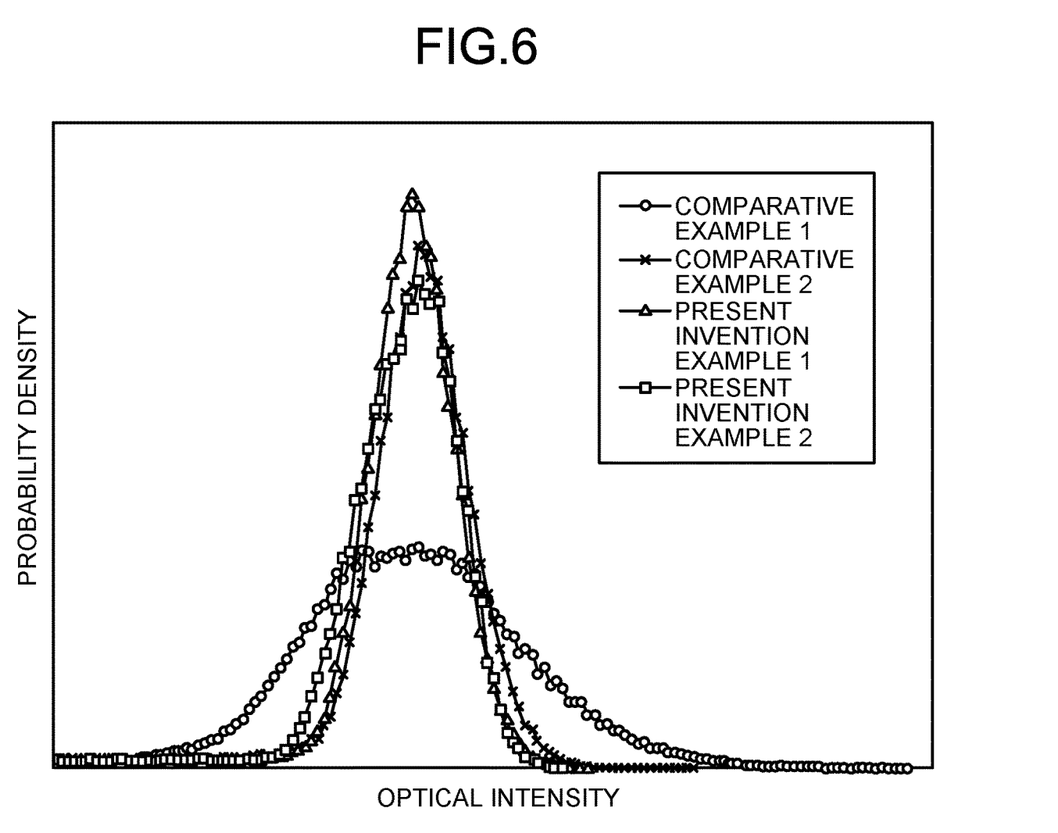
FIG. 6 is a graph for explaining the relationship of the number of ablation-related laser diodes and the number of optical combiners with the laser light flatness in a laser apparatus with the optical combiners connected in a cascade state, according to working examples of the present disclosure.
Figure 7:
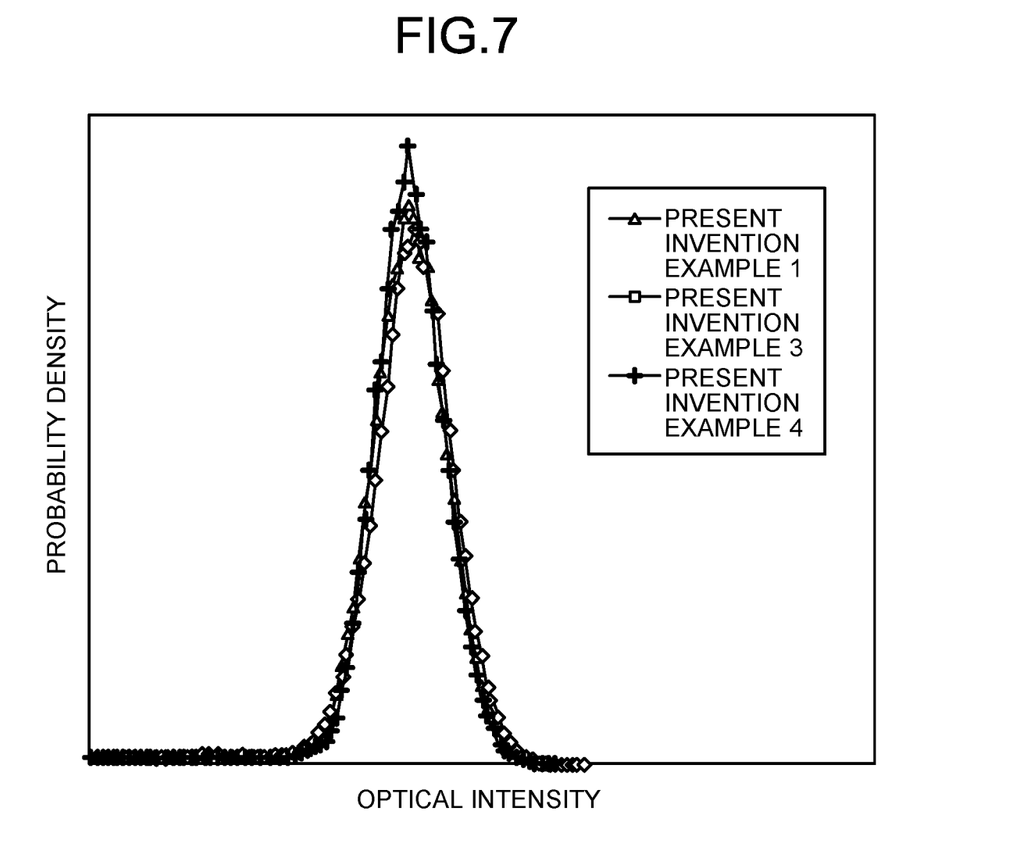
FIG. 7 is a graph for explaining the relationship of the number of ablation-related laser diodes and the number of optical combiners with the laser light flatness in a laser apparatus with the optical combiners connected in a cascade state, according to working examples of the present disclosure.

Next, an explanation will be given of the relationship of the positions of ablation-related LDs and the number of optical combiners with the laser light flatness in a laser apparatus in which the optical combiners are connected in a cascade state, with reference to FIGS. 6 and 7. In these working examples, the optical intensity maps of laser lights, emitted from laser apparatuses with a plurality of configurations, were created, and the optical intensity data of the respective pixels of these optical intensity maps were combined to form a histogram, by which the graph illustrated in FIGS. 6 and 7 were created. In FIGS. 6 and 7, the horizontal axis indicates the optical intensity of a laser light, and the vertical axis indicates the probability density of having the optical intensity indicated on the horizontal axis. Therefore, in FIGS. 6 and 7, the laser light flatness becomes higher as the graph stands more upright, and the laser light flatness becomes lower as the graph is flatter.

Here, the comparative examples 1 and 2 and the present disclosure examples 1 to 4 in FIGS. 6 and 7 represent the following configurations, respectively.

The comparative example 1 represents a configuration in which only one ablation-related LD is arranged and no optical combiner is included.

The comparative example 2 represents a configuration in which two ablation-related LDs are connected to one optical combiner.

The present disclosure example 1 represents the configuration of FIG. 3.

The present disclosure example 2 represents the configuration of FIG. 4.

The present disclosure example 3 represents the configuration of FIG. 1.

The present disclosure example 4 represents the configuration of FIG. 5.

As illustrated in FIGS. 6 and 7, by comparing the comparative example 1 including no optical combiner with the comparative example 2 and the present disclosure examples 1 to 4 each of which includes an optical combiner, it can be seen that the flatness of the latter examples is higher. Further, by comparing the comparative example 2 including one optical combiner with the present disclosure examples 1, 3, and 4 each of which includes two optical combiners, it can be seen that the flatness of the latter examples is higher. Further, by comparing the present disclosure examples 1, 3, and 4 each of which includes two optical combiners with the present disclosure example 2 including three optical combiners, it can be seen that the flatness of the former examples is higher. Further, by comparing the comparative examples 1 and 2 with the present disclosure examples 1 to 4, it can be seen that the present disclosure example 4, which includes two optical combiners and an asymmetric tap coupler connected to the optical combiner in the rearmost stage, is the highest in the flatness.

In the above descriptions, the laser apparatus according to each of the embodiments of the present disclosure has been specifically explained in the form for implementing the disclosure and by taking working examples. However, the gist of the present disclosure is not limited to these descriptions, and should be broadly interpreted on the basis of the scope of the claims. Further, it goes without saying that various changes, modifications, and so forth based on these descriptions are also included in the gist of the present disclosure.

For example, in the third embodiment described above, an explanation has been given of the configuration in which the number of optical combiners 12 connected in a cascade state is three (see FIG. 4). However, in order to obtain a laser light with more higher-order modes, the number of optical combiners 12 may be set to four or more.

Further, in the embodiments described above, the explanations have been given on the assumption that the laser apparatus 1, 1A, 1B, or 1C is used for a medical catheter or the like, but the application of the laser apparatus 1, 1A, 1B, or 1C is not limited to the medical use.

The present disclosure is suitable for the application to a laser apparatus that provides a medical treatment by irradiating a target area, such as an affected area, with a laser light from the tip of an optical fiber inside a catheter.

According to an embodiment, it is possible to improve the laser light flatness without requiring a large space, by connecting a plurality of optical combiners in a cascade state.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

The invention claimed is:

1. A laser apparatus comprising:
two or more laser diodes and two or more optical combiners, wherein
output sides of the two or more laser diodes are directly connected to respective input sides of optical combiners different from each other, and
an output side of one optical combiner is connected to an input side of an optical combiner other than the one optical combiner.

2. The laser apparatus according to claim 1, wherein optical fibers used in input ports and output ports of the two or more optical combiners are multi-mode optical fibers.

3. The laser apparatus according to claim 1, wherein the two or more optical combiners are 2:1 optical combiners.

4. The laser apparatus according to claim 1, wherein the two or more optical combiners include first and second optical combiners, of which
an output side of the first optical combiner is connected to an input side of the second optical combiner.

5. The laser apparatus according to claim 1, wherein the two or more optical combiners include first, second, and third optical combiners, of which
an output side of the first optical combiner is connected to an input side of the second optical combiner, and
an output side of the second optical combiner is connected to an input side of the third optical combiner.

6. The laser according to claim 1, wherein optical fibers used in input ports and output ports of the one or more laser diodes are multi-mode optical fibers.

7. The laser apparatus according to claim 1, wherein a number of the two or more laser diodes is smaller than the total number of input ports of the two or more optical combiners.

8. The laser apparatus according to claim 1, comprising an asymmetric tap coupler, wherein
an input side of the asymmetric tap coupler is connected to an output side of one of the two or more optical combiners, which is arranged in a rearmost stage.

9. A laser apparatus comprising:
one or more laser diodes, two or more optical combiners and an asymmetric tap coupler, wherein
output sides of the one or more laser diodes are connected to an input side of one optical combiner among the two or more optical combiners,
an output side of the one optical combiner is connected to an input side of an optical combiner other than the one optical combiner, and
optical fibers used in input ports and output ports of the two or more optical combiners are multi-mode opticl fibers,
wherein flatness of laser light output from the optical combiner is improved compared with flatness of laser light when the optical combiner does nto exist,
an inptu side of the saymmetric tap coupler is connected to an output side of one of the two or more optical combiners, which is arranged in a rearmost stage,
a higher-order mode light excited by the optical combiner is removed by the asymmetric tap coupler, and
a ring beam is formed from the position of the tap port.

* * * * *